(12) United States Patent
Subramanian et al.

(10) Patent No.: US 12,702,866 B2
(45) Date of Patent: Aug. 11, 2026

(54) RADIOTHERAPY APPLICATOR SYSTEM

(71) Applicant: Best Medical International, Inc., Springfield, VA (US)

(72) Inventors: Manny R. Subramanian, Frederick, MD (US); Jagannadha Rao Nibhanupudy, Glenn Dale, MD (US); Rohit V. Mehta, Clifton, VA (US); Rashmi Amin, Springfield, VA (US)

(73) Assignee: Best Medical International, Inc., Springfield, VA (US)

( * ) Notice: Subject to any disclaimer, the term of this patent is extended or adjusted under 35 U.S.C. 154(b) by 974 days.

(21) Appl. No.: 17/910,594

(22) PCT Filed: Mar. 12, 2020

(86) PCT No.: PCT/US2020/022378
§ 371 (c)(1),
(2) Date: Sep. 9, 2022

(87) PCT Pub. No.: WO2021/183130
PCT Pub. Date: Sep. 16, 2021

(65) Prior Publication Data

US 2023/0126722 A1 Apr. 27, 2023

(51) Int. Cl.
*A61N 5/10* (2006.01)

(52) U.S. Cl.
CPC ......... *A61N 5/1007* (2013.01); *A61N 5/1028* (2013.01); *A61N 2005/1012* (2013.01); *A61N 2005/1094* (2013.01)

(58) Field of Classification Search
CPC .......................................... A61N 5/1001–1029
See application file for complete search history.

(56) References Cited

U.S. PATENT DOCUMENTS 5,772,574 A * 6/1998 Nanko ................. A61N 5/1007 600/1
6,059,713 A 5/2000 Urick et al.
(Continued)

FOREIGN PATENT DOCUMENTS

EP 0292630 A1 * 11/1988 ........... A61N 5/1001

OTHER PUBLICATIONS

International Search Report for PCT/US2020/0022378, dated May 28, 2020.

*Primary Examiner* — Thaddeus B Cox
(74) *Attorney, Agent, or Firm* — McGinn IP Law Group, PLLC

(57) ABSTRACT

The radiotherapy applicator system includes an applicator pad adapted to cover a target area of a patient for radiation treatment. One or more spaced channels extend through a length of the applicator pad. Each channel receives a catheter sleeve, and an elongate seed line is selectively inserted into a corresponding catheter sleeve. Each seed line contains one or more radioactive seeds and spacers arranged in a predetermined pattern along the length of the seed line. The seed lines within the applicator pad form an array of a predetermined, geometric treatment pattern of seeds covering the target area, the treatment pattern predetermined from a treatment plan for that target area and the patient. Shielding is provided to protect staff administering the treatment and non-target areas from harmful levels of radiation exposure. The radiotherapy applicator system is reusable for multi-session treatment and may be provided as a customized kit.

23 Claims, 7 Drawing Sheets

(56) References Cited

U.S. PATENT DOCUMENTS

| | | | |
|---|---|---|---|
| 6,330,479 | B1 | 12/2001 | Stauffer |
| 6,458,070 | B1 * | 10/2002 | Waksman ............ A61N 5/1007 600/3 |
| 2004/0054249 | A1 | 3/2004 | Visscher et al. |
| 2004/0109823 | A1 | 6/2004 | Kaplan |
| 2004/0147836 | A1 * | 7/2004 | Lagendijk ............ A61N 5/1007 600/7 |
| 2005/0251235 | A1 | 11/2005 | Schlorff et al. |
| 2011/0060391 | A1 | 3/2011 | Unetich et al. |
| 2012/0157748 | A1 | 6/2012 | Sioshansi et al. |
| 2017/0165500 | A1 * | 6/2017 | Flynn ..................... A61N 5/103 |

* cited by examiner 32
30
31
10
20
22
21
50
40
42
41
40

20
21

20
21

22
223
21
20
223

120
123
121

RADIOTHERAPY APPLICATOR SYSTEM

FIELD OF THE INVENTION

The present invention relates to medical devices for radiotherapy procedures and treatment, and particularly to a radiotherapy applicator system that provides a cost-effective and tailored means of treating one or more cancerous sites on a patient.

BACKGROUND

Currently, millions in the USA suffer from or diagnosed with a type of melanoma or skin cancer. Treatments for most skin cancers range from surgery, medication, radiation, or even chemotherapy depending on the stage of the disease.

Radiation treatment for skin cancer or tumor can be a relatively costly endeavor for a patient, as well as the provider, such as oncologists and dermatologists. A typical radiation treatment involves utilizing a linear accelerator (LINAC) as the source of a radiation beam for the tumor and a collimator for shaping and controlling the beam and the beam's intensity on the tumor or target. This is generally considered as an external beam radiation therapy, which is aptly applicable for most cases of skin cancer, since the tumor typically lies on the surface of the skin or shallow within a subcutaneous layer. A facility that administers such radiation treatments must also have adequate shielding to protect the staff administering the therapy. The equipment to facilitate the radiation treatment can be rather expensive for a provider, such as a dermatologist or oncologist, to afford, and most have to collaborate with a major hospital or facility to share the hospital's resources for such treatments. Moreover, this type of typical radiation treatment, in addition to being relatively expensive, is generally a more complex method of destroying the tumor when the circumstances may call for a more nuanced, less intense radiation exposure. It is the goal of most, if not all, radiation treatments to accurately and effectively treat the tumor while limiting or minimizing radiation exposure to healthy tissue around the cancerous tumor, as well as provide an effective and cost effective treatment, without unduly jeopardizing the health of the surrounding tissue. Furthermore, some treatment facilities, such as those in less developed countries, may not have the finances or resources for such radiotherapy equipment.

In light of the above, it would be a benefit in the medical arts to provide a radiotherapy device or system to treat skin cancer or similar cancerous tumors in an economical manner without resorting to expensive radiotherapy treatment apparatus and shielding. Thus, in addressing this need, a radiotherapy applicator system has been developed to provide an economical treatment option for tumors and skin cancers.

SUMMARY OF THE INVENTION

Embodiments of a radiotherapy applicator system desirably include, for example, an applicator pad adapted to cover a target area of a patient for radiation treatment. One or more spaced channels extend through a length of the applicator pad. Each channel receives a catheter sleeve, and an elongate seed line is selectively inserted into a corresponding catheter sleeve. Each seed line contains one or more radioactive seeds and spacers arranged in a predetermined pattern along the length of the seed line. The seed lines within the applicator pad form an array of a predetermined, geometric treatment pattern of seeds adapted to cover the target area, the treatment pattern predetermined from a treatment plan for that target area and the patient. Shielding is also desirably provided to protect staff administering the treatment from harmful levels of radiation exposure. The radiotherapy applicator system is reusable for a multi-session treatment and may be provided as a customized kit tailored for a specific patient.

Embodiments of the invention further include methods of treating tumors by determining a radiation treatment plan for radiotherapy treatment of a target area of a patient by embodiments of the radiotherapy applicator system in one or more predetermined sessions for the radiotherapy treatment.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Figure 1:
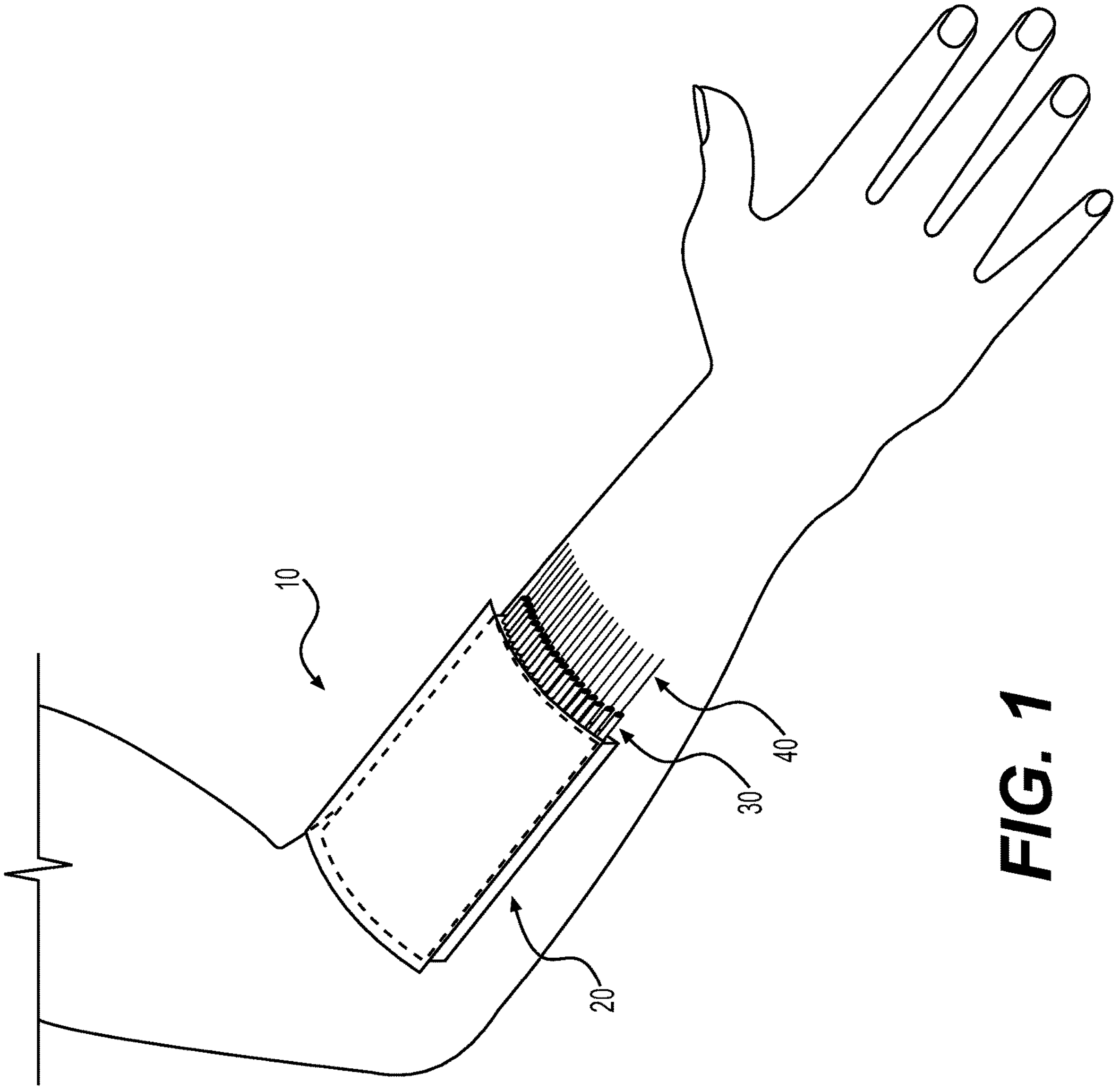
FIG. 1 is an environmental, perspective view of an embodiment of a radiotherapy applicator system according to the present invention.
Figure 2:
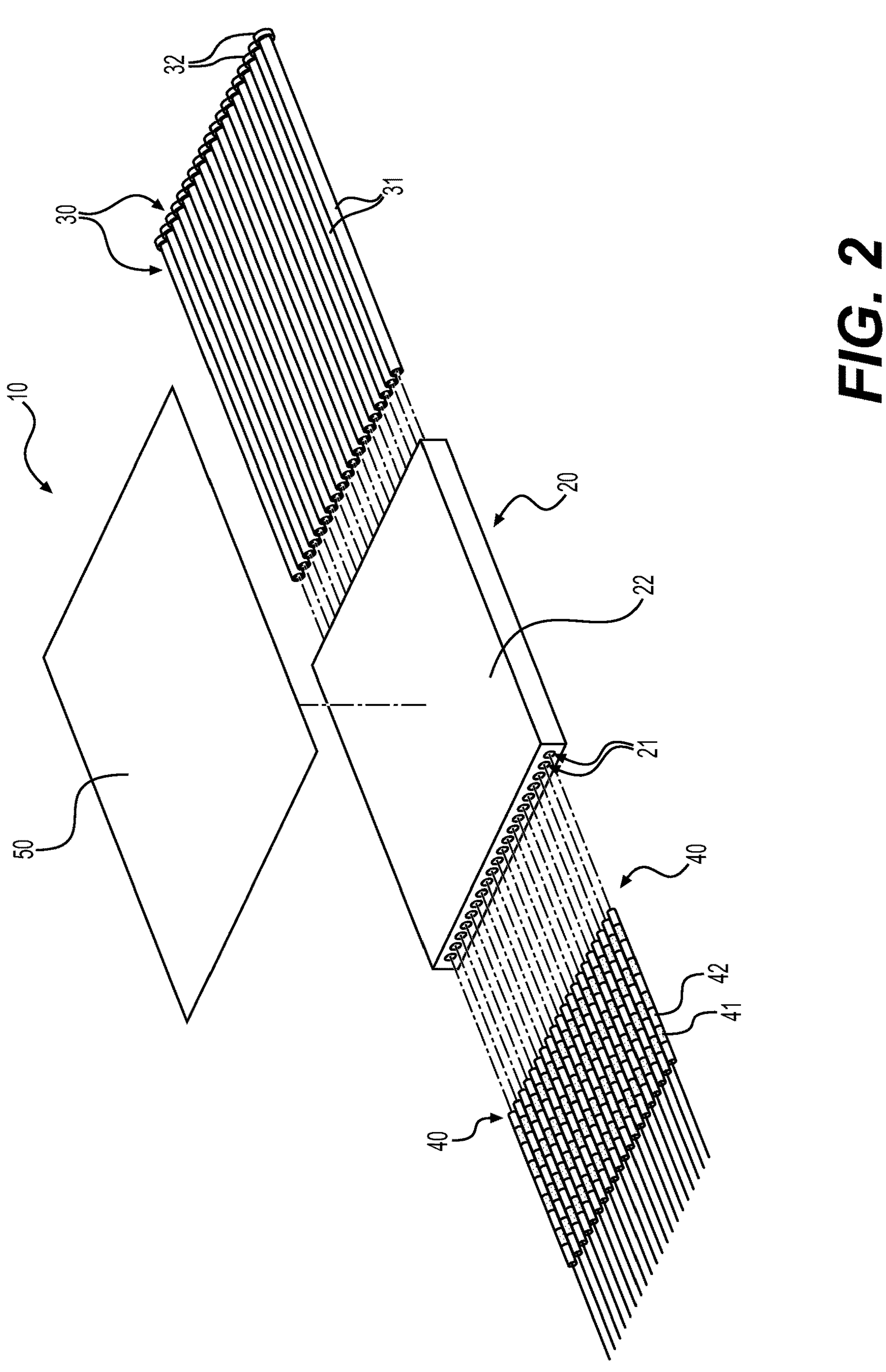
FIG. 2 is an exploded view of the embodiment of a radiotherapy applicator system shown in FIG. 1 according to the present invention.

An embodiment of a radiotherapy applicator system, generally referred to by the reference number 10 in the drawings, provides an economic radiation treatment apparatus for treating tumors, such as from skin cancer, in a gentle and relatively simple manner compared to conventional radiotherapy treatment with minimal impact on surrounding healthy tissue. As best seen in FIGS. 1 and 2, the radiotherapy applicator system 10 includes an applicator pad 20 for placement over a target area, one or more catheter sleeves 30 inserted through the applicator pad 20, one or more seed lines 40 threaded through corresponding catheter sleeves 30, and a shielding 50 wrapped over the applicator pad 20 to protect others and the patient receiving the treatment from undesirable radiation exposure.

Referring to FIGS. 1, 2, 3A, 3B, and 3C, the applicator pad 20 is desirably configured as an elongate, flexible rectangular body 22 having one or more channels 21 extending along a length of the body 22 and equidistantly spaced along a width of the body 22. Each channel 21 serves as a mount for insertably holding a corresponding catheter sleeve 30 therein. In an embodiment, the applicator pad 20 is desirably provided with nineteen channels 21, although the number of channels 21 can be any suitable number of channels 21, as can depend on the use or application, and should not be construed in a limiting sense.

The body 22 of the applicator pad 20 is desirably constructed from a suitable bio-compatible material, such as silicone, a relatively hypoallergenic, bio-compatible material with suitable flexibility for conforming to the contours of the patient at the location of the target area. Though flexible, it is also desirable that the applicator pad 20 maintains a degree of stiffness so as to retain its general shape even when flexed. This combination of flexibility and stiffness permits the applicator pad 20 to function as a base for installing working components of the radiotherapy applicator system 10, especially the catheter sleeves 30 and the seed lines 40, in a predetermined spaced manner. Other suitable materials for the body 22 of the applicator pad 20 include homopolymers and copolymers made from polystyrene, polyethylene, polypropylene, polyamides, polyesters, polyanhydrides, poly-ortho esters, poly-amido amines, and poly β-amino esters. Any deviation in spacing due to flex in the body 22 will be within acceptable limits as long as the seed pattern conforms to the target shape, details of which will be discussed hereinbelow.

In an embodiment, the applicator pad 20 is desirably about 10 cm by 10 cm with a thickness of about 1.65 mm to 2.65 mm. Each channel 21 desirably has a diameter of about 1.7 mm suitably large enough for selective insertion of the catheter sleeve 30 from one end of the applicator pad 20. It is to be recognized that these dimensions are exemplary of one embodiment. They can be changed depending on application and use of the user, and should not be construed in a limiting sense.

Figure 6:
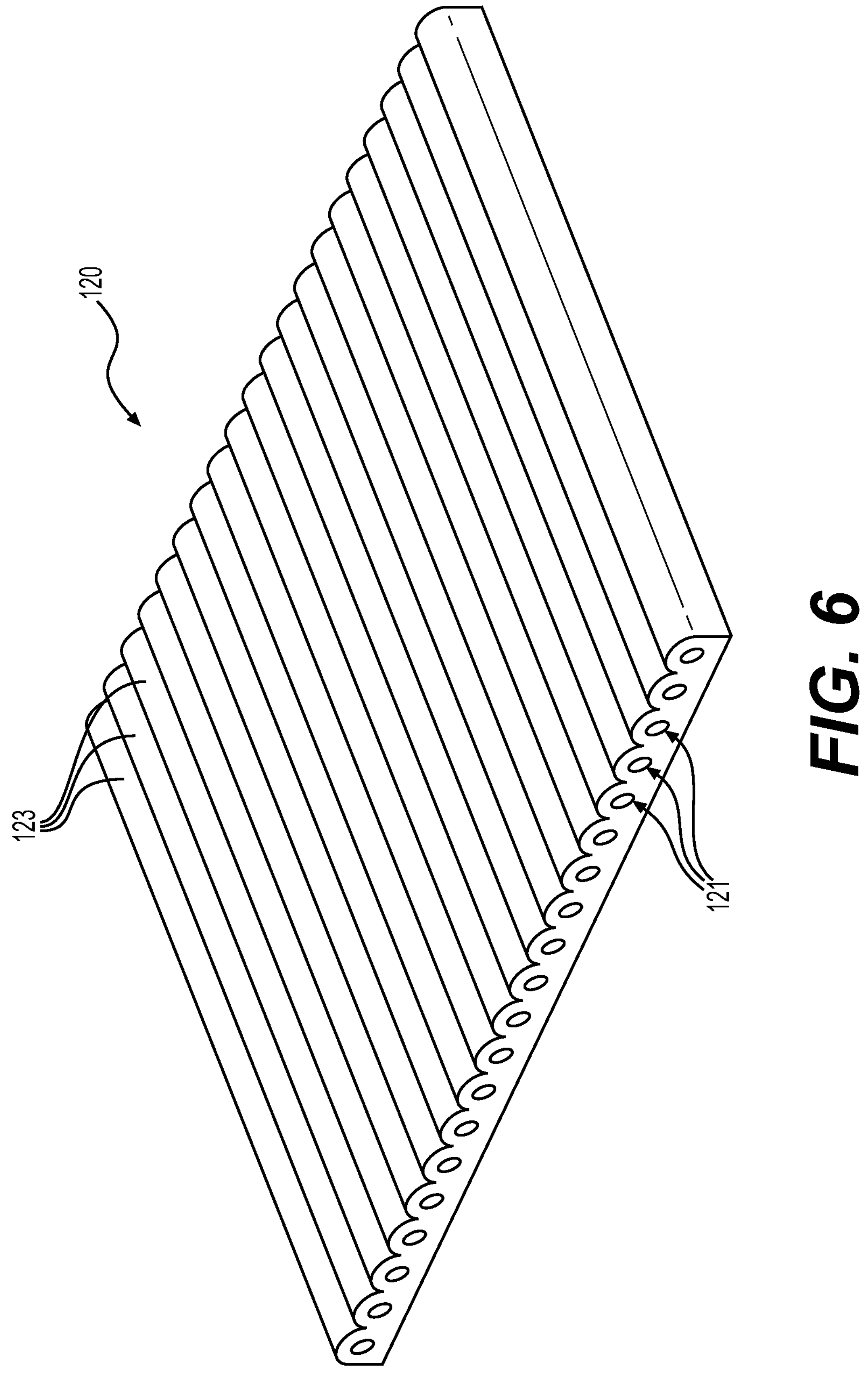
FIG. 6 is a perspective view of another embodiment of an applicator pad for the radiotherapy applicator system shown in FIGS. 1 and 2 according to the present invention.

Another embodiment of an applicator pad is an applicator pad 120 is shown in FIG. 6. In this embodiment, the top or upper half of the applicator pad 120 is provided with a plurality of corrugations 123 extending along a length of the applicator pad 120. Each corrugation 123 is coaxial with a corresponding channel 121. The bottom of the applicator pad 120 is flat in the same manner as the applicator pad 20. The corrugations 123 of the applicator pad 120 provide enhanced flexibility enabling the applicator pad 120 to bend easily to thereby ease covering and wrapping around the target area on the patient. In both embodiments, the bottom of the applicator pad 20, 120 is desirably flat since this is the portion of the applicator pad 20, 120 touching the patient's skin. In all other respects, the applicator pad 120 is substantially the same as the applicator pad 20.

Figure 4:
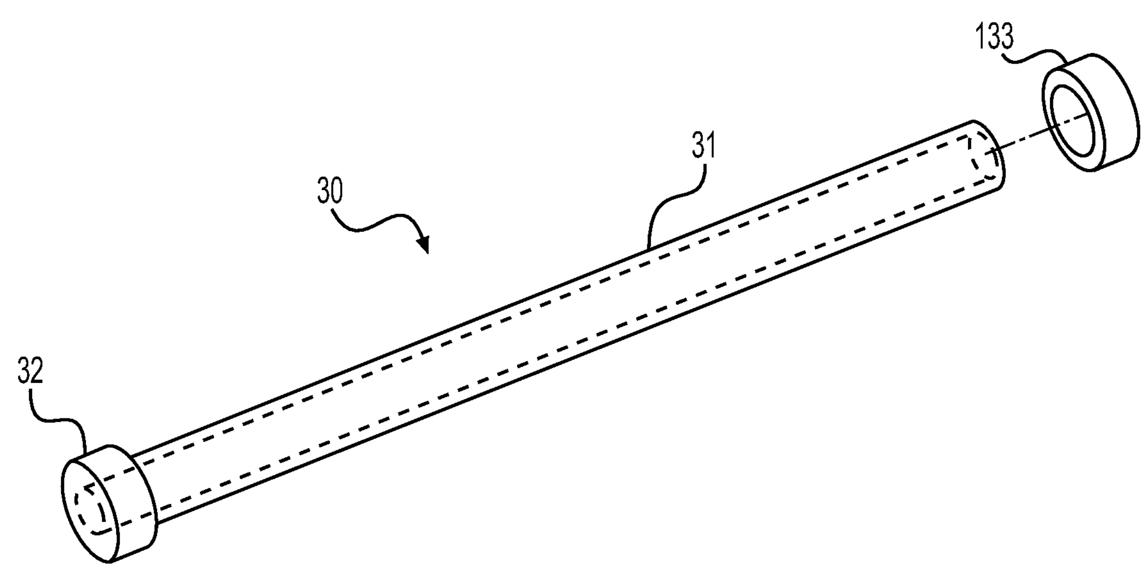
FIG. 4 is a perspective view of a catheter sleeve for the radiotherapy applicator system shown in FIGS. 1 and 2 according to the present invention.

As best seen in FIGS. 2 and 4, each catheter sleeve 30 includes an elongate tube section 31 and an endcap 32 covering one end of the tube section 31 leaving the opposite end of the tube section 31 open. Each catheter sleeve 30 is desirably constructed from nylon or other suitable material. However, other types of plastics, such as polyethylene terephthalate, polyvinyl chloride, polypropylene, polystyrene, and other suitable medical grade plastics or plasticized material may also be used. The elongate tube section 31 desirably has a diameter about the same as the diameter of the channel 21 so as to be securely seated therein when assembled. The length of the elongate tube section 31 is desirably longer than the length of the applicator pad 20. Since the corresponding seed line 40 providing the radioactive material, such as a radioactive seed, for the treatment is desirably longer than even the catheter sleeve 30, the relatively long length of the elongate tube section 31 insures that the seed line 40 will be securely contained therein when assembled. Thus, when assembled, a portion of each seed line 40 extends out of the open end of the catheter sleeve 30, such as illustrated in FIG. 1, which enables the user to easily grasp that extended portion to remove or unsheathe the seed line 40 for subsequent disposal after use. It is to be understood, however, that these dimensions or relative dimensions of the channel 21, 121, the tube section 31, applicator pad 20, 120 and the seed line 40 can be varied depending on application and use of the applicator pad 20, 120, as long as minimal tolerances are maintained between the channels 21, 121 and the tube sections 31 lying within, and the length of the tube sections 31 are suitably long enough to secure subsequent insertion of the seed lines 40.

The endcap 32 is desirably larger in diameter than the diameter of the tube section 31 so as to enable the endcap 32 to lie flat and abut against one end of the applicator pad 20, 120 or wedged into that end of the applicator pad 20 and be flush therewith when inserted into a corresponding channel 21, 121. The endcap 32 provides a back stop for one end of the seed line 40 to abut against when the seed line 40 is threaded and inserted within the tube section 31. Additionally, the tube section 31 serves as a sheath for easy insertion of the seed line 40 while protecting the same within the applicator pad 20, 120.

The radiotherapy applicator system 10 is desirably configured to be tailored to the needs of each individual patient or treatment area since the tumor to be treated is generally unique or specific to the patient or treatment area, such as in severity or a stage of the tumor, as well as the physical dimensions of the tumor or treatment area, such as its form and shape, for example. To accommodate these differences, the radiotherapy applicator system 10 desirably provides an array of one or more seed lines 40 with a unique or specific arrangement of radioactive seeds 41 and spacers 42 mounted along respective cables or wires 43 for the particular use or application involved in the treatment.

Figure 5:
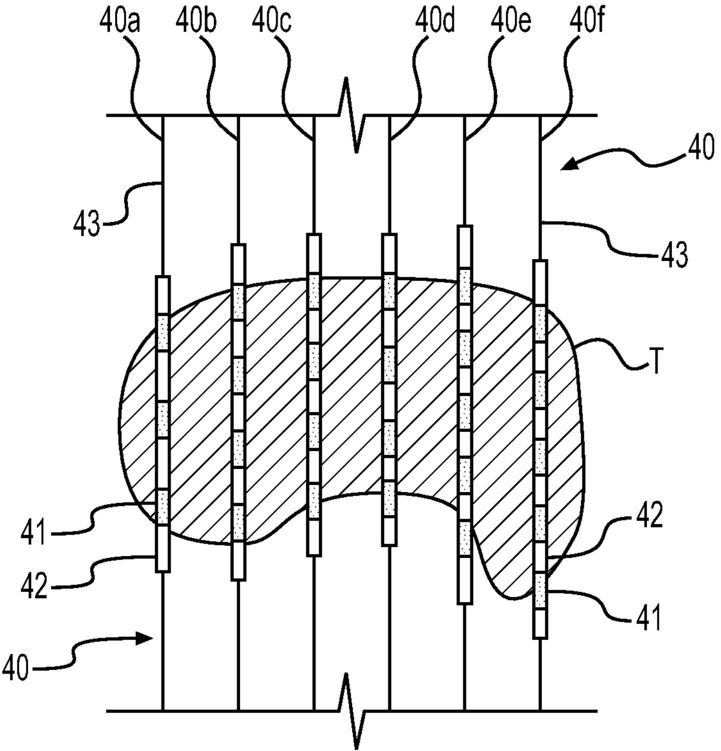
FIG. 5 is a schematic view of an arrangement of seed lines configured to treat a specific target tumor according to the present invention, the applicator pad having been removed in the figure for description and clarity.

For example, as best seen in FIGS. 2 and 5, a tumor T has an irregular shape along a coronal or horizontal plane. Based upon a predetermined radiation therapy plan developed to treat this tumor T, seeds 41 (represented by the shaded or dark sections) and spacers 42 (represented by white sections) on each seed line 40 have been arranged to provide an optimal approximation of an irradiation pattern required by the treatment plan to treat the tumor with the radioactive seeds 41. The spacers 42 can be made of suitable plastic or plasticized material, such as homopolymers and copolymers made from polystyrene, polyethylene, polypropylene, polyamides, polyesters, polyanhydrides, poly-ortho esters, poly-amido amines, and poly β-amino esters, for example, as can depend on the use or application. Each seed 41 defines a radioactive hot spot, and the arrangement of seeds 41 and spacers 42 on each seed line 40 provides radiation that covers a specific portion of the tumor T along this arrangement of seeds 41 and spacers 42 of the corresponding seed line 40. The radioactive seeds 41 can be of a suitable radioactive material to deliver a radiation dose for a treatment, such as Iodine-125, Palladium-103, Iridium-192, Gold-198, or Cobalt-57, for example.

In the schematic example shown in FIG. 5, there are six seed lines 40*a*, 40*b*, 40*c*, 40*d*, 40*e*, 40*f* spaced across the tumor T. It can be seen that each seed line 40*a*, 40*b*, 40*b*, 40*c*, 40*d*, 40*e*, 40*f* includes a specific number of alternating seeds 41 and spacers 42 forming a set of seeds and spacers for the corresponding seed line 40*a*, 40*b*, 40*c*, 40*d*, 40*e*, 40*f*, and the relative position of each set of alternating seeds 41 and spacers 42 may be different from one seed line 40 to the next due to the unique or specific shape of the tumor T. For example, the seed line 40*a* contains an alternating pattern set of three seeds 41 and four spacers 42 to irradiate the leftmost portion of the tumor T. However, the subsequent seed line 40*b* contains an alternating pattern set of four seeds 41 and five spacers 42 so as to provide radiation coverage for the relatively longer vertical portion of the tumor T next to the seed line 40*a*. Due to the longer length of this portion of the tumor T, the set of seeds 41 and spacers 42 for the seed line 40*b* is correspondingly longer. The remaining seeds lines 40*c*, 40*d*, 40*e*, 40*f* are also similarly arranged with their own specific set of alternating sets of seeds 41 and spacers 42 to cover their corresponding portion of the tumor T. It can be seen from the above that the specific array is focused, in terms of radiation exposure, on the tumor while minimizing exposure to the healthy surrounding tissue.

It is to be understood that the above is exemplary of a possible array of seed lines 40 and sets of seeds 41 and spacers 42. Depending on the characteristics of the tumor T to be treated, any number of seed lines 40 and arrangement of seeds 41 and spacers 42 can be configured so as to accommodate the particular tumor T. Moreover, a specific set of seeds 41 and spacers 42 need not be alternating. The set can include two or more spacers 42 or seeds 41 arranged side-by-side along a corresponding wire 43 that carries or supports a set of the seeds 41 and the spacers 42. Furthermore, the dimensions of the seeds 41 and the spacers 42 can be varied depend on use and application. In an embodiment, the spacers 42 can be constructed from nylon or plastic, or other suitable material, similar to the catheter sleeve 30. Additionally, the wire 43 is desirably constructed from tantalum, tungsten, aluminum, gold, titanium, stainless steel, nitinol, and combinations thereof, or other suitable materials or metals, as can depend on the use or application, and should not be construed in a limiting sense.

While the seed lines 40 provide the necessary radiation, the person administering the radiation treatment and areas of the patient not being in the treatment area must also be shielded from that radiation dose from the radioactive seeds 41. In that regard, the radiotherapy applicator system 10 includes a shielding 50. As best seen in FIGS. 1 and 2, the shielding 50 is desirably a flat thin sheet of radiation blocking material with a width and a length greater than the width and the length of the applicator pad 20, 120. The larger dimensions and relative thinness of the shielding 50 enables the shielding 50 to easily cover and wrap around the edges of the applicator pad 20 similar in manner to an aluminum foil wrap to thereby block any radiation emanating upwardly and outwardly from the radioactive seeds 41 of the inserted seed lines 40 during use and substantially confine the irradiation to the general target area or treatment area, such as for the tumor T or for skin cancer. The material of the shielding 50 is desirably constructed from lead, tin, copper, zinc, or combinations thereof. Any other suitable material capable of effectively blocking radiation may also be used, as can depend on the use or application, for example.

Figure 7:
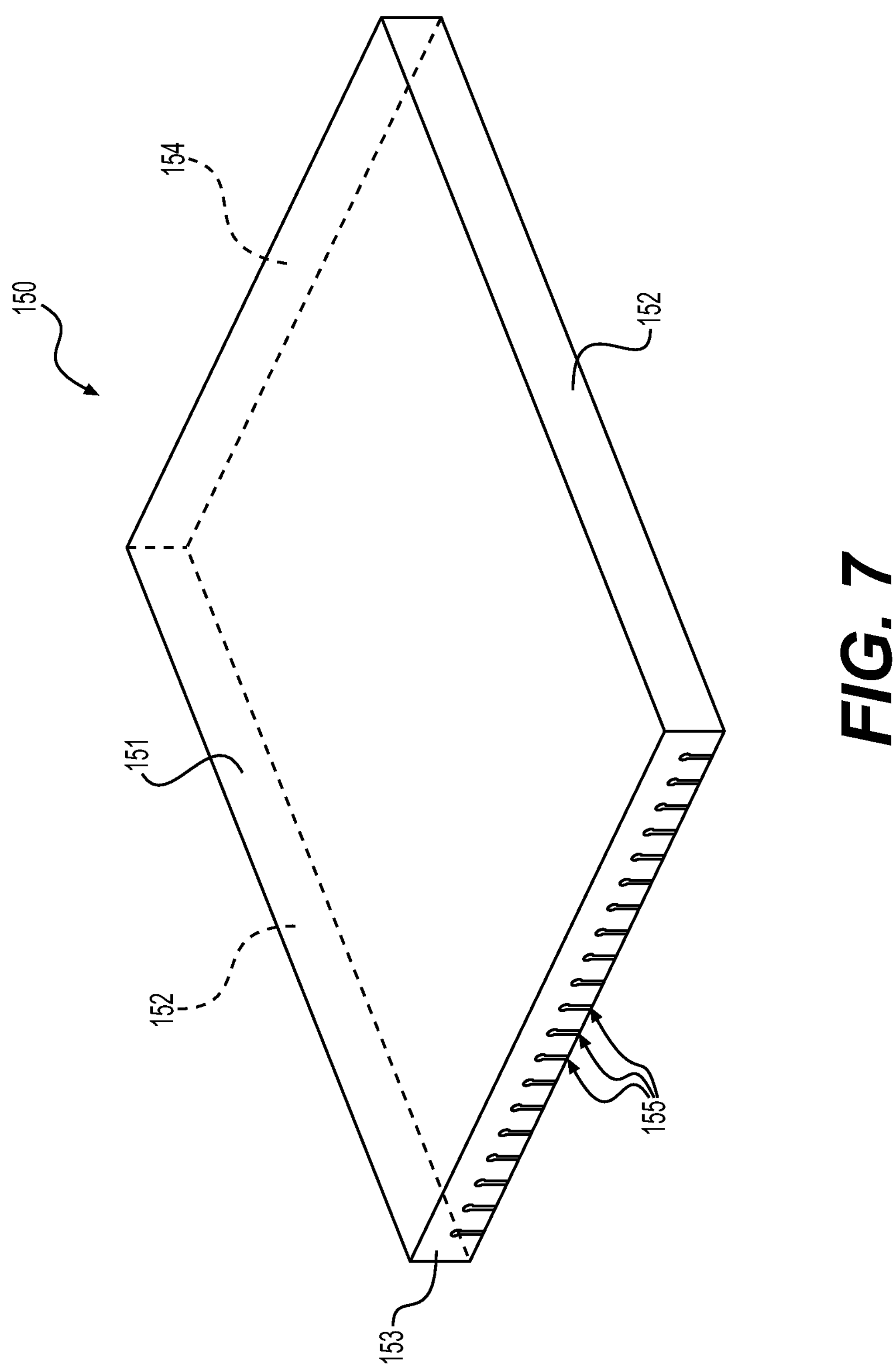
FIG. 7 is a perspective view of another embodiment of a shielding for the radiotherapy applicator system shown in FIGS. 1 and 2 according to the present invention.

Another embodiment of a shielding 150 is shown in FIG. 7. In this embodiment, the shielding 150 is constructed as a formed, rectangular or square cover or cap that fits over the applicator pad 20, 120 similar in shape to a typical box cover. The shielding 150 can be of similar thickness or thicker than the shielding 50. The thickness of the shielding 150 should be suitably thick to maintain the general desired shape while also allowing a degree of flexure. The shielding 150 includes a top panel 151, side panels 152, a front panel 153 extending between one end of the side panels 152, and a back panel 154 extending between the opposite ends of the side panels 152. The dimensions of the shielding 150, i.e. width, length, and height, are desirably greater than the dimensions of the applicator pad 20, 120, which enables the shielding 150 to be easily placed over the applicator pad 20, 120 during assembly.

To accommodate the seed lines 40 extending from one end of the applicator pad 20, 120 during use, the front panel 153 is provided with one or more pass-through slots 155. The pass-through slots 155 each desirably extends from the bottom of the front panel 153 towards the top, terminating about midway or more on the front panel 153. The pass-through slots 155 are also desirably keyhole shaped, although the slots 155 can be of other suitable shapes as can depend on the use or application. When assembled, the pass-through slots 155 serve as gaps for the extended portion of the seed lines 40, such as for a portion of the wire 43 and/or a portion of the tube section 31, to pass through as the shielding 150 is lowered onto the applicator pad 20, 120. The desired keyhole shape facilitates accommodation of the portion of tube section 31 of the catheter sleeves 30 that extend past one end of the applicator pad 20, 120, since the tube section 31 is larger in diameter than the diameter of the wire 43.

Since the shielding 150 is desirably substantially the same shape as the applicator pad 20, 120, the shielding 150 is faster and easier to assemble in the sense that the shielding 150 does not require wrapping around the applicator pad 20, 120 compared to the shielding 50. Additionally, when the applicator pad 20, 120 is flexed or bent around the target area or treatment area during use such as in treating the tumor T or skin cancer, the pass-through slots 155 enable the shielding 150 to also correspondingly flex or bend therewith by permitting the portions of the front panel 153 between the pass-through slots 155 to overlap a certain amount. The relative thinness of the shielding 150 and the flexure provided thereby enables the shielding 150 to conform to the contours of the target area, such as of the tumor T, and the corresponding flex of the applicator pad 20, 120 during use.

The following describes the radiotherapy applicator system 10 in use referencing the embodiment shown in FIGS. 1-4. Initially, the radiotherapy applicator system 10 is desirably provided as a package or kit containing all the components required to treat the patient through one or more radiation treatment sessions, such as the applicator pad 20, catheter sleeves 30, tube sections 31, endcaps 32, seed lines 40 including the radioactive seeds 41, spacers 42 and wires 43, and the shielding 50. Additionally, a predetermined treatment plan to treat the target area or treatment area, such as to treat the tumor T or skin cancer, for the patient is already known. Since the treatment plan is predetermined, it is desirable to provide the applicator pad 20, catheter sleeves 30, and seed lines 40 as a preassembled component of the radiotherapy applicator system 10 in most instances. This preassembled component would be shielded for handling purposes. The predetermined treatment plan forms a basis upon which the dimensions of the applicator pad 20 (at least in terms of the length and width), and the number of channels 21, catheter sleeves 30, and seed lines 40 will be configured. The array of seed lines 40 with various sets of radioactive seeds 41 and spacers 42 is tailored to the target area or treatment area of the patient due to the unique or specific characteristics of the tumor T or skin cancer to be treated. Such a preassembled component of the radiotherapy applicator system 10 ensures that the specific array of seeds 41 and spacers 42 will be configured correctly and conform to the treatment plan as long as the provider or manufacturer has the correct data and proper checks are in place for the arrangement of the array of the seed lines 40. Since the seed lines 40 are radioactive components due to the seeds 41 thereon, the seed lines 40 can also be provided separately with proper labels and/or indicia (not shown) to enable the same to be handled in accordance with regulations regarding radioactive materials as well as placement in the applicator pad 20. In this instance, the seed lines 40 would be assembled on site by the user, and the labels and/or indicia will assist the user in correct placement of the seed lines 40 within the corresponding channels 21.

During use, the applicator pad 20 with the corresponding seed lines 40 inserted therein is placed over the target area of the patient, such as in corresponding relation to the tumor T or skin cancer to be treated. The flexible nature of the applicator pad 20 enables the applicator pad 20 to conform to the contours of the patient at the target area. The user then wraps and covers the applicator pad 20 with the shielding 50 so as to minimize radiation exposure to the user or to areas of the patient outside of the treatment area. After a predetermined length of time dictated by the session parameters, the radiotherapy applicator system 10 is removed from the target area.

At times, a successful or effective radiation treatment may require multiple sessions, and the radiotherapy applicator system 10 is designed to be reusable for such purposes. The radiotherapy applicator system 10 or just the seed lines 40 can be stored in a properly shielded environment after each use. When the radiation treatment is completely finished through one or more sessions, the seed lines 40 can be removed and sent back to the manufacturer for subsequent disposal in accordance with regulations or protocols for proper handling of radioactive materials.

It is to be understood that the radiotherapy applicator system 10 can encompass a variety of embodiments. For example, the applicator pad 20, 120 can be provided in a variety of suitable shapes or configurations, such as a rectangle, or square shape or configuration, or other suitable shapes or configurations, as can depend on the use or application. The shape or configuration of the applicator pad 20, 120 can, for example, also be circular, polygonal, curvilinear, or a specific shape corresponding to the unique shape of the tumor to be treated. Such configurations of the applicator pad 20, 120 can enable closer accommodation of unusual shaped tumors, reduce material consumption for manufacture, and/or add a further tailored element for treating the tumor or skin cancer, for example.

Figures 3A, 3B, 3C:
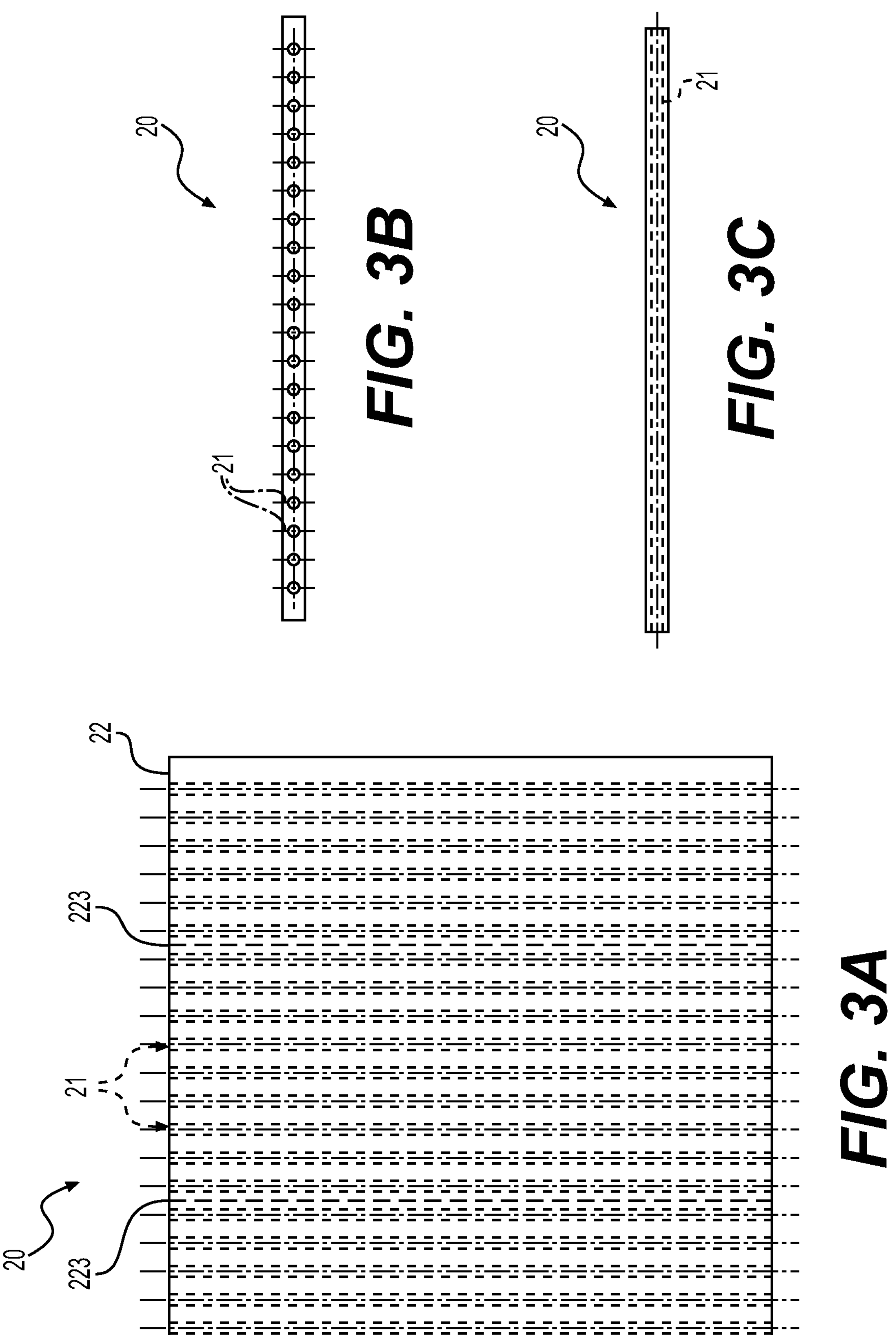
FIG. 3A is a plan view of an applicator pad for the radiotherapy applicator system shown in FIGS. 1 and 2 according to the present invention.
FIG. 3B is a front view of the applicator pad shown in FIG. 3A according to the present invention.
FIG. 3C is a side view of the applicator pad shown in FIG. 3A according to the present invention.

As illustrated in FIG. 3A, the body of the applicator pad 20, 120 can also be provided with one or more perforations 223 formed at predetermined spaced intervals along the width of the applicator pad 20, 120. These perforations 223 would extend along the length of the applicator pad 20, 120 and be disposed between adjacent channels 21, 121. The perforations 223 can enable the user to tear the applicator pad 20, 120 along the perforations 223, which permits the applicator pad 20, 120 to be constructed in relatively long sheets and torn to a desired size whether it is from the manufacturer or on site by the user.

In other embodiments, the catheter sleeve 30 can be provided with two endcaps 32, 133. As illustrated in FIG. 4, one endcap 32 is disposed at one end of the tube section 31 and the other endcap 133 is disposed at the opposite end of the tube section 31. The other endcap 133 would include an open end rather than a closed end to enable insertion therethrough of the seed line 40. The two endcaps 32, 133 can be constructed from or include suitable echogenic and/or radio-opaque materials. This allows the endcaps 32, 133 to be seen by conventional imaging means, such as ultrasonic imagers, CT scans, MRI scanners, and X-rays to thereby assist in monitoring and/or evaluating relative positions of the seed lines 40 to the target area, such as the tumor T. Moreover, the endcaps 32, 133 can be provided in other geometric shapes or configurations, such as a sphere, square block, polygonal shape, or other suitable shapes, in addition to the disk shape shown in the Figures, as can depend on the use or application, and should not be construed in a limiting sense.

Figure 8:
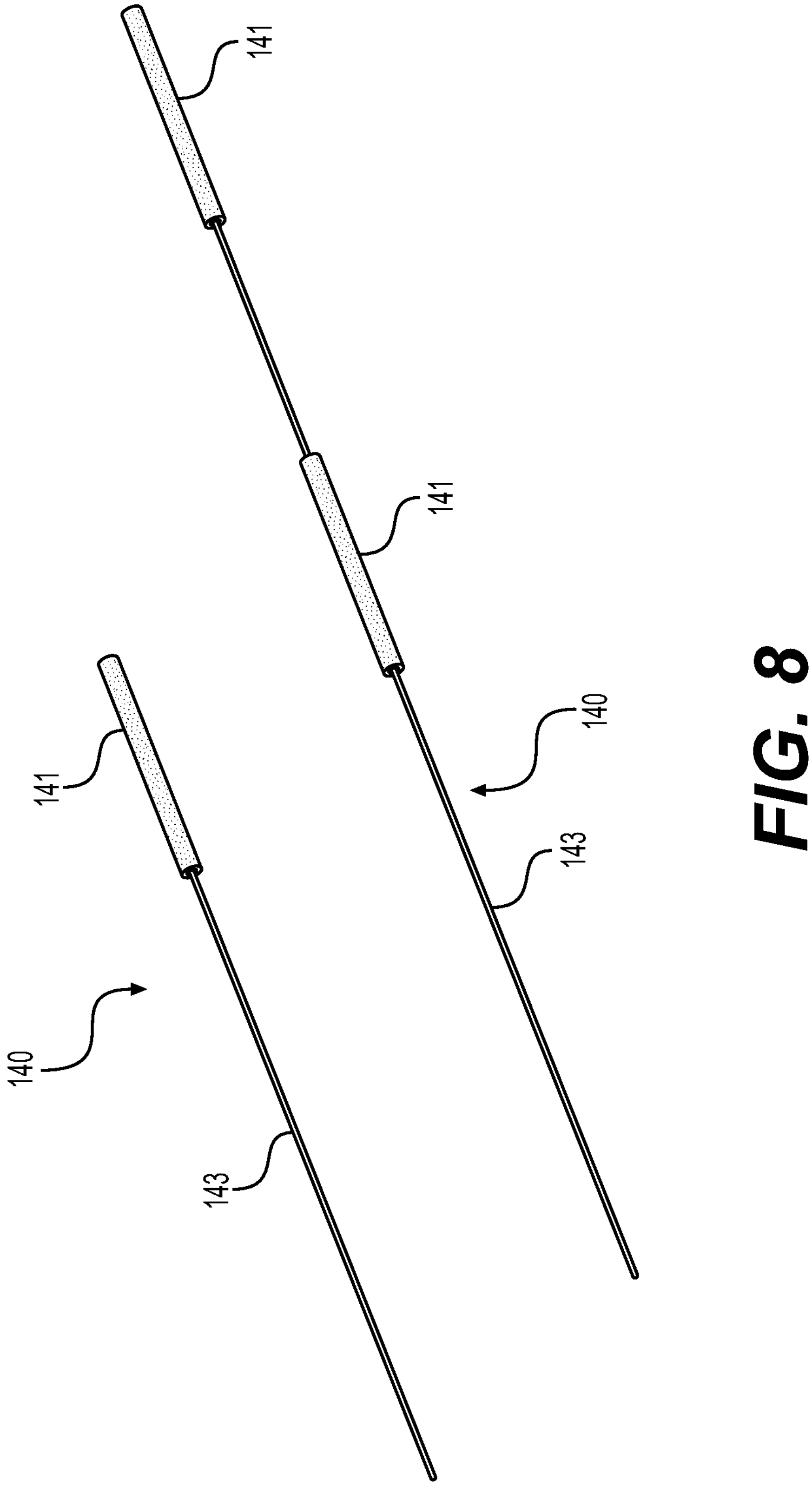
FIG. 8 is a perspective view of an embodiment of a seed line for the radiotherapy applicator system according to the present invention.

Another embodiment of a seed line 140 is illustrated in FIG. 8. In this embodiment, the seed line 140 includes one or more radioactive cables or wires 143 with one or more radioactive portions 141 formed thereon. Each of the radioactive portions 141 is desirably wire-like in shape and appearance. Sections between adjacent radioactive portions 141 can be non-radioactive. As with the seed lines 40, one or more of the seed lines 140 define an array of radioactive hot spots vis-à-vis the radioactive portions 141, when assembled, for irradiating the target area on the patient in accordance with a predetermined radiation treatment plan for delivery of a radioactive dose to treat the target area, such as the tumor T. Also, each of the radioactive portions 141 on each of the radioactive wires 143 can be at a same or different radiation intensity level, for example.

As with the seed lines 40, each radioactive wire 143 is configured to be selectively mounted within a tube section 31 on a corresponding catheter sleeve 30, with the elongate catheter sleeve 30 being mounted within a corresponding channel 21, 121 of the applicator pad 20, 120. Also, each radioactive wire 143 is desirably long so that when assembled, each radioactive portion 141 extends into the tube section 31 of the catheter sleeve 30 and a portion of the remainder of the radioactive wire 143 extends out of the corresponding catheter sleeve 30 to facilitate selective removal or insertion of the wire 143 from the corresponding catheter sleeve 30. The radioactive material in or formed as part of the wire 143 for the radioactive portions 141 can include Iodine-125, Palladium-103, Iridium-192, Gold-198 or Cobalt-57, for example. It should be noted that only the radioactive portions 141 are radioactive while the remainder of the radioactive wire 143 is non-radioactive. The non-radioactive portions of the radioactive wire 143 can be formed of various suitable materials or metals, such as tantalum, tungsten, aluminum, gold, titanium, stainless steel, nitinol, and combinations thereof, or other suitable materials or metals, as can depend on the use or application, and should not be construed in a limiting sense.

Therefore, in embodiments having the radioactive wire 143, instead of providing a specific set of seeds 41 and spacers 42 for each seed line 40 associated with a corresponding wire 43, the one or more radioactive wires 143 can provide the necessary predetermined array or arrays of radioactive hot spots for the radiotherapy treatment with generally fewer components. Such integral construction of the radioactive material in the radioactive wire 143 can be a simpler means of obtaining a seed line with the desired radioactive profile to the extent that it involves less parts to assemble.

Thus, it can be seen that the radiotherapy applicator system 10 provides a cost-effective and gentler means of treating cancerous tumors, especially those resulting from skin cancer. All the components of the radiotherapy applicator system 10 are relatively inexpensive compared to LINACs used in most conventional radiation treatments, and the specific configuration of the applicator pad 20, 120 and the seed lines 40 can be easily tailored for individual patients. Though the radiotherapy applicator system 10 is generally used for topical treatments, the radiotherapy applicator system 10 can also be used for internal treatments, as well.

It is to be understood that the present invention is not limited to the embodiments described above, but encompasses any and all embodiments within the scope of the following claims.

We claim:

1. A radiotherapy applicator system, comprising:

a flexible applicator pad configured to be placed on or over and conform to contours of a target area of a patient for a radiotherapy treatment, the flexible applicator pad having a body with opposing ends and a plurality of elongate channels within the flexible applicator pad, each elongate channel extending between the opposing ends of the body;

a plurality of elongate catheter sleeves each configured to be selectively mounted within a corresponding elongate channel within the flexible applicator pad, each elongate catheter sleeve configured to have an endcap at least at one end;

a plurality of elongate seed lines, each elongate seed line configured for delivery of a radioactive dose to treat the target area, each elongate seed line being configured to be selectively mounted within a corresponding elongate catheter sleeve mounted within a corresponding elongate channel within the flexible applicator pad, each elongate seed line having at least one radioactive portion, and each elongate seed line having a portion extending out of the corresponding elongate catheter sleeve when assembled to facilitate selective removal or insertion of the elongate seed line from the corresponding elongate catheter sleeve; and a shielding configured to cover the flexible applicator pad during use to minimize radiation exposure to a user administering the radiotherapy treatment or to the patient receiving the radiotherapy treatment with the radiotherapy applicator system, wherein each elongate seed line is adapted to provide radiation that covers a specific portion of the target area, and wherein the plurality of elongate seed lines, when each of the plurality of elongate seed lines is mounted within a corresponding elongate catheter sleeve mounted within a corresponding elongate channel within the flexible applicator pad, provides an arrangement of elongate seed lines defining an array of hot spots forming a predetermined, geometric treatment pattern for irradiating the target area in accordance with a predetermined radiation treatment plan for the patient.

2. The radiotherapy applicator system according to claim 1, wherein said body of said flexible applicator pad comprises a substantially rectangular block.

3. The radiotherapy applicator system according to claim 2, wherein said body of said flexible applicator pad is constructed from silicone.

4. The radiotherapy applicator system according to claim 1, wherein said body of said flexible applicator pad comprises a substantially square block.

5. The radiotherapy applicator system according to claim 4, wherein said body of said flexible applicator pad is constructed from silicone.

6. The radiotherapy applicator system according to claim 4, wherein said substantially square block comprises an upper half and a flat bottom, said upper half having a plurality of elongate corrugations extending between opposing ends of said body of the flexible applicator pad, each elongate corrugation being coaxial with a corresponding elongate channel in said flexible applicator pad.

7. The radiotherapy applicator system according to claim 1, wherein each said elongate catheter sleeve comprises an elongate tube section and a said endcap covering one end of said tube section, an opposite end of the tube section being open to receive a corresponding elongate seed line therein, said tube section having a given diameter and said endcap having a given diameter.

8. The radiotherapy applicator system according to claim 7, wherein the diameter of said endcap is greater than the diameter of said tube section.

9. The radiotherapy applicator system according to claim 7, wherein each said elongate catheter sleeve is constructed from material selected from the group consisting of nylon, polyethylene terephthalate, polyvinyl chloride, polypropylene, polystyrene, and medical grade plastic.

10. The radiotherapy applicator system according to claim 1, wherein each said elongate seed line of the plurality of elongate seed lines comprises an elongate wire having a set of at least one radioactive seed and at least one spacer arranged thereon in a predetermined elongate pattern, each said radioactive seed defining a said radioactive portion.

11. The radiotherapy applicator system according to claim 10, wherein each said elongate seed line comprises a corresponding said predetermined elongate pattern, each said predetermined elongate pattern of at least one radioactive seed and at least one spacer on a corresponding said elongate seed line configured to irradiate a portion of said target area, at least one of said predetermined elongate patterns being different from another of said predetermined elongate patterns to accommodate differences in a shape and a form of said target area along a length of said predetermined elongate patterns.

12. The radiotherapy applicator system according to claim 10, wherein said elongate wire is constructed from material selected from the group consisting of tantalum, tungsten, aluminum, gold, titanium, stainless steel, nitinol, and combinations thereof.

13. The radiotherapy applicator system according to claim 1, wherein said shielding comprises a flat thin sheet of radiation blocking material, said flat sheet having a width and a length greater than a width and a length of said flexible applicator pad.

14. The radiotherapy applicator system according to claim 13, wherein said radiation blocking material is selected from the group consisting of lead, tin, copper, zinc, and combinations thereof.

15. The radiotherapy applicator system according to claim 1, wherein said shielding comprises a formed, rectangular or square shaped cover adapted to fit over the flexible applicator pad, said formed rectangular or square shaped cover having a top panel, opposing side panels extending downwardly from said top panel, a front panel extending between one end of said side panels, and a back panel extending between an opposite end of said side panels.

16. The radiotherapy applicator system according to claim 15, wherein said front panel includes a plurality of pass-through slots, each said pass-through slot extending from a bottom of said front panel towards a top of said front panel and terminating about midway on said front panel, each said pass-through slot being configured to allow passage of a portion of a corresponding elongate seed line when assembled.

17. The radiotherapy applicator system according to claim 16, wherein each said pass-through slot comprises a keyhole shape.

18. The radiotherapy applicator system according to claim 1, wherein each said elongate seed line of the plurality of elongate seed lines comprises an elongate radioactive wire having at least one portion of a radioactive material formed therewith, each said portion having said radioactive material defining a said radioactive portion, said radioactive material arranged on said elongate radioactive wire in a predetermined elongate pattern.

19. The radiotherapy applicator system according to claim 18, wherein each said predetermined elongate pattern formed by said at least one portion of the radioactive material configured to irradiate a portion of said target area, and at least one of said predetermined elongate patterns being different from another of said predetermined elongate patterns to accommodate differences in a shape and a form of said target area along a length of said at least one of said predetermined elongate patterns.

20. The radiotherapy applicator system according to claim 1, wherein said flexible applicator pad includes one or more perforations formed at predetermined spaced intervals along a width of the flexible applicator pad and each perforation extending along a length of the flexible applicator pad, each perforation configured to enable the flexible applicator pad to be torn along a corresponding said perforation to form a desired size of the flexible applicator pad for the radiotherapy treatment.

21. A radiotherapy applicator system kit for a radiotherapy treatment, comprising:

- a flexible applicator pad configured to be placed on or over and conform to contours of a target area of a patient for the radiotherapy treatment, the flexible applicator pad having a body with opposing ends and a plurality of elongate channels within the flexible applicator pad, each elongate channel each extending between the opposing ends of the body;
- a plurality of elongate catheter sleeves each configured to be selectively mounted within a corresponding elongate channel within the flexible applicator pad, each elongate catheter sleeve configured to have an endcap at one end;
- a plurality of elongate seed lines, each elongate seed line configured to be selectively mounted within a corresponding elongate catheter sleeve mounted within a corresponding elongate channel within the flexible applicator pad, each elongate seed line having mounted thereon a set of at least one radioactive seed and at least one spacer, each elongate seed line having a length greater than a length of the corresponding elongate catheter sleeve in order to have a portion of the elongate seed line extending out of the corresponding elongate catheter sleeve when assembled for selective removal or insertion of the elongate seed line from the corresponding elongate catheter sleeve; and
- a shielding configured to cover the flexible applicator pad during use to minimize radiation exposure to a user administering the radiotherapy treatment or to the patient receiving the radiotherapy treatment,
- wherein each elongate seed line having the at least one radioactive seed and the at least one spacer is adapted to provide radiation that covers a specific portion of the target area, and
- wherein the plurality of elongate seed lines, when each of the plurality of elongate seed lines is mounted within a corresponding elongate catheter sleeve mounted within a corresponding elongate channel within the flexible applicator pad, provides an arrangement of elongate seed lines defining an array of hot spots forming a predetermined, geometric treatment pattern, when assembled, for irradiating the target area on the patient in accordance with a predetermined radiation treatment plan for the patient.

22. A method for radiotherapy treatment, comprising the steps of:

- determining a radiation treatment plan for a target area of a patient, the target area being unique in shape and form to the patient, the treatment plan including one or more predetermined sessions for the radiotherapy treatment;
- providing a radiotherapy applicator system, comprising:
  - a flexible applicator pad configured to be placed on or over and conform to contours of the target area of the patient, the flexible applicator pad having a body with opposing ends and a plurality of elongate channels within the flexible applicator pad, each elongate channel extending between the opposing ends of the body;
  - a plurality of elongate catheter sleeves each configured to be selectively mounted within a corresponding elongate channel within the flexible applicator pad, each elongate catheter sleeve configured to have an endcap at one end;
  - a plurality of elongate seed lines, each elongate seed line configured to be selectively mounted within a corresponding elongate catheter sleeve mounted within a corresponding elongate channel within the flexible applicator pad, each elongate seed line having a set of at least one radioactive seed and at least one spacer mounted thereon, each elongate seed line having a portion extending out of the corresponding elongate catheter sleeve when assembled to facilitate selective removal or insertion of the elongate seed line from the corresponding elongate catheter sleeve; and
  - a shielding configured to cover the flexible applicator pad during use to minimize radiation exposure to a user administering the radiotherapy treatment and to the patient receiving the radiotherapy treatment,
  - wherein each elongate seed line having the set of at least one radioactive seed and at least one spacer mounted thereon is adapted to provide radiation that covers a specific portion of the target area, and
  - wherein the plurality of elongate seed lines, when each of the plurality of elongate seed lines is mounted within a corresponding elongate catheter sleeve mounted within a corresponding elongate channel within the flexible applicator pad, provides an arrangement of elongate seed lines defining an array of hot spots forming a predetermined, geometric treatment pattern for irradiating the target area of the patient in accordance with the radiation treatment plan for the patient;
- placing the flexible applicator pad with the plurality of elongate catheter sleeves and the plurality of elongate seed lines respectively mounted therein on or over the target area;
- covering the flexible applicator pad with the shielding to protect the user and areas of the patient other than the target area from radiation exposure;

treating the target area for a given period of time with radiation from the plurality of radioactive seeds respectively mounted on the plurality of elongate seed lines as required by the treatment plan;

removing the radiotherapy applicator system from the target area at the end of a said session for the radiotherapy treatment; and selectively repeating the placing, covering, treating, and removing steps for multiple sessions, when the radiation treatment plan provides for a plurality of sessions for the radiotherapy treatment.

23. The method for radiotherapy treatment according to claim 22, further comprising the step of:

storing the plurality of elongate seed lines in a shielded environment after each session.

* * * * *